United States Patent [19]
Gorria et al.

[11] Patent Number: 5,408,104
[45] Date of Patent: Apr. 18, 1995

[54] APPARATUS AND PROCESS WITH AN ANNULAR FLUORESCENT TUBE FOR DETECTION IN A MOVING MODE OF SURFACE DEFECTS ON LONG METALLIC PRODUCTS

[75] Inventors: Patrick Gorria, St.Sernin du Bois; Hafid Jender, Dijon; Michel Paindavoine, Le Creusot; Frédéric Truchetet, Marmagne; Pascal Gerard, Montbard; Phu-An Ngo, Aulnoye, all of France

[73] Assignee: Valinox, Boulogne-Billancourt, France

[21] Appl. No.: 74,404

[22] Filed: Jun. 10, 1993

[30] Foreign Application Priority Data

Jun. 10, 1992 [FR] France .................. 92 06987

[51] Int. Cl.⁶ ............................. G01N 21/88
[52] U.S. Cl. .................. 250/572; 250/208.1; 382/8; 348/132
[58] Field of Search ........... 250/572, 562, 571, 223 R, 250/208.1; 356/426, 240, 430; 209/586, 538; 382/8, 22, 54; 348/132

[56] References Cited
U.S. PATENT DOCUMENTS 4,817,184 3/1989 Thomason et al. ............... 382/8
5,086,232 2/1992 Maguire et al. ................. 250/572

FOREIGN PATENT DOCUMENTS 3412503 10/1985 Germany .
2224831 5/1990 United Kingdom .
WO92/08967 5/1992 WIPO .

OTHER PUBLICATIONS

Iron and Steel Engineer, vol. 67, No. 5, May 1990, pp. 26–29, M. Ho, "Surface Inspection System With Defect Classification".

Primary Examiner—David C. Nelms
Assistant Examiner—Que T. Le
Attorney, Agent, or Firm—Oblon, Spivak, McClelland, Maier & Neustadt

[57] ABSTRACT

An apparatus and a process for detecting surface defects on moving long metallic products utilizing linear CCD cameras for effecting exposures at successive times t1, t2,t3 ... Tn. A processing device calculates differences observed for each pixel or assemble of pixels at the successive times and any variations in the differences makes it possible to detect defects and the extent of the defects. The use of thresholds allows for reduction in the background noise and different orientations of the optical axis of the camera permit the detection of different types of defects.

24 Claims, 5 Drawing Sheets

APPARATUS AND PROCESS WITH AN ANNULAR FLUORESCENT TUBE FOR DETECTION IN A MOVING MODE OF SURFACE DEFECTS ON LONG METALLIC PRODUCTS

BACKGROUND OF THE INVENTION

The apparatus and the process the subject of the present invention concern detection in a moving mode of surface defects on long metallic products such as tubes, bars, strips or various sections.

DISCUSSION OF THE INVENTION

Different means are known for detecting in a moving mode defects on long metallic products. Such means involve the use for example of the emission of ultrasound or the production of eddy currents. Those means suffer from the disadvantage of not permitting detection of surface defects such as scratches or scores of small depth, highly localized depressions, changes in shade caused by localised chemical attacks or oxidation phenomena or deposits of foreign materials of small thickness.

The use of a linear C.C.D. camera for the inspection of metallic strips is described in the work entitled "Automated visual inspection" by B. G. Batchelor, D. A. Hill and D. C. Hodgson (I.F.S. Publications Ltd. U.K. 1985). In accordance with the examples given on pages 288 to 289, it is possible to detect holes in thin strips. For that purpose, as a receiving surface, use is made of bar portions comprising 256, 512 or 1024 pixels, depending on the width of the strip. The lighting thereof can be effected by reflection or transmission, which gives a much higher degree of sensitivity. The possibility of detecting and/or measuring defects in appearance such as coloured stains or blemishes and also scratches or scores or differences in level is not envisaged.

Research has been carried on into the possibility of developing an apparatus for automatic inspection which makes it possible to detect in a moving mode and preferably in a single passage, on long metallic products, localised defects in colour such as stains, of a dieter which is at least equal to about 1 mm, or more extended defects in colour, for example yellows or blues, and also defects in relief such as scratches, fine cracks or abrasion scores or impressions caused by impacts or holes of small diameter or any other surface defect giving rise to a slight change in level or a noticeable change in colour.

SUMMARY OF THE INVENTION

The process and the apparatus for the automatic monitoring of long products by artificial vision which are the subject of the present invention make it possible to detect those different types of defects, to provide for quantitative measurement of the magnitude thereof and to suppress or considerably attenuate the influence of the general appearance of the surface to be monitored.

The process and the apparatus concern the detection of defects on the surface of long metallic products such as tubes, bars, shaped members or strips. They make it possible to monitor defects of all kinds such as cracks, pits or scores, depressions or changes in level caused by impacts or other causes, surface deposits and also stains or blemishes of all dimensions and all natures such as for example oxidation colours.

The process and the apparatus for automatic inspection by artificial vision permit continuous examination of a long product in a moving mode at a speed which can easily attain 1 m/s. The process employed has the particularity that it makes it possible to distinguish true defects from slight variations in the signals received by the detection devices, such variations being considered as normal and being due to an array of minor causes without real significance in terms of the quality of the surface of the products. The process also makes it possible not to take account of certain defects of dimensions which are too small to have an influence on the characteristics of use of the products.

The process comprises using at least one linear camera of the CCD type whose optical axis is directed towards the surface of the long product to be monitored. A lighting means lights the region of the product, towards which the camera is oriented. The sensitive surface thereof is formed by a linear bar of N pixels which is oriented transversely with respect to the axis of movement of the product. A suitable optical means permits focusing of the camera onto the lit surface of the product. An entrainment means permits the product to be caused to move along the axis of movement at the desired speed.

Data acquisition and processing means make it possible, at equal successive time intervals "t" to measure numerical values "niv i" corresponding for each pixel to the amount of light received at the end of the time "t". In order to limit the number of elementary operations, it is possible to determine "niv i" on a series of pixels N1 which is selected from the N pixels of the bar.

In the case for example of a bar made up of 256 pixels, it is for example possible to limit the number N1 to 100 and to distribute those 100 pixels in a regular fashion in such a way that they cover in respect of width the entire region of the image of the product which is to be monitored, irrespective of the dimension of the product to be monitored within given limits.

The acquisition and processing means are used in such a way that, at equal successive intervals of time "t", it is possible to measure for each pixel "i" a level "niv i" whose numerical value corresponds to the amount of light received during the time "t". The highest values "niv i" are obtained for an excellent surface state of the product which reflects, like a mirror, the light coming from the lighting means. Stains or blemishes absorb a more or less substantial amount of light, while the various changes in level or scratches deflect or disperse the light.

An effective means for determining those defects involves measuring the differences between the numerical values "niv i" of each pixel which are successively measured after two exposure times such as t1, t2. It is then possible to determine the sum of those differences for all of the N1 pixels, the variation in the value of that sum making it possible to detect the appearance or disappearance of defects.

In order better to observe the variation in such differences, it is possible to produce the sum of their absolute values for all of the N1 pixels in accordance with the following relationship:

$$\text{Cumulative total } 1 = \sum_{i=1}^{i=N1} |niv(i, t2) - niv(i, t1)|$$

Producing the sum in terms of an absolute value of those differences over the length of a bar, at two successive times, makes it possible to detect the appearance or the disappearance of defects. However a substantial degree of dispersion is observed in respect of those differences which are totalled in that way, due to minor variations in the reflective capability of the metallic surface and small stains or blemishes without any real influence on the quality of the product.

On the basis of two successive values of "cumulative total 1" which are determined between exposure times such as t1, t2, t3, it is possible to calculate a combined difference value P1 such that:

$$P1 = |Cumulative\ total\ 1\ (t3\text{-}t2) - Cumulative\ total\ 1\ (t2\text{-}t1)|$$

P1—being taken as an absolute value.

There has been developed a method for processing of the data supplied by those differences, which has been found to be of much greater effectiveness.

In accordance with that method, the numerical value "niv i" for the difference calculations is limited to a maximum value, referred to as the "grey threshold", all the higher values being brought to that threshold. In addition, the cumulative total of the differences is produced not in terms of absolute value but as an algebraic value, subtraction of the values "niv i" always being effected in the same direction with respect to the successive exposure times.

The sum of the algebraic values of those differences for all of the N1 pixels is expressed by the following relationship:

$$Cumulative\ total\ 2 = \sum_{i=1}^{i=N1} [(niv\ i\ threshold,\ t2) - (niv\ i\ threshold,\ t1)]$$

Then, on the basis of two successive values of "Cumulative total 2" which are determined between exposure times such as t1, t2, t3, a combined difference value P2 is calculated such that:

$$P2 = |Cumulative\ total\ 2\ (t3\text{-}t2) - Cumulative\ total\ 2\ (t2\text{-}t1)|$$

That value P2 which results from the algebraic subtraction of the two values of cumulative total 2 is taken in terms of absolute value. It makes it possible to locate and better identify the defects, in respect of which it is possible to assess the extension and evolution in time.

In accordance with the invention, to achieve the maximum degree of sensitivity in the observation of stains or blemishes and other defects in terms of colour, it is necessary to use a camera whose optical axis is at an angle which is as small as possible to a plane perpendicular to the axis of movement. Preferably the angle formed by that optical axis and the plane perpendicular to the axis of movement is limited to not more than 30° for the observation of such stains or blemishes or other defects in colours.

Still in accordance with the invention, for the observation of relief defects such as changes in level or other surface defects such as scratches, cracks, scores or the like, the best results are obtained with an inclination of the camera such that its optical axis is inclined at at least 60° with respect to the plane perpendicular to the axis of movement.

Preferably, in order to detect in a single pass all of the defects which have just been referred to above, with the maximum degree of sensitivity, the apparatus according to the invention comprises at least two cameras whose respective optical axes are oriented one at not more than 30° and the other at not less than 60° with respect to a plane perpendicular to the axis of movement.

As indicated above, it is desirable to limit the number of pixels in respect of which the values "niv i" are processed in order to standardize and accelerate the data processing operation. If for example N1 is limited to 100 in the case of a bar of 256 pixels, only one pixel out of two will be taken if the image covers 200 pixels. The width of a pixel being about $13 \times 10^{-6}$ m, there is no substantial loss in detection precision. The system will be arranged so that, depending on the dimension of the products being monitored, the image covers at least 100 pixels in respect of which, in this case, all the values "niv i" will be processed.

The duration of the exposure time is selected in dependence on the lighting of the cameras, that varying with all other things being equal with the angle of the optical axis of the camera to a plane perpendicular to the axis of movement. The duration of the exposure time also varies with the speed of movement of the product and the size of the minimum defects which are to be detected.

For applications of the apparatus and the process to the detection of defects on long rotationally symmetrical products, two groups of cameras are preferably used. A first group preferably comprises four linear cameras of CCD type, the optical axis of which is not inclined by more than about 30° with respect to the plane perpendicular to the axis of movement of the product. Advantageously that angle of inclination is limited to about 15°. Those four cameras are distributed around the axis of movement at about 90° from each other, with their optical axes converging on the axis of movement. Advantageously, the focal length and the aperture are selected in such a way as to form on the bar of pixels the image of at least one quarter of the perimeter of the product with preferably a certain overlap of the edges of the images produced by the adjacent cameras.

The lighting means used is advantageously an annular fluorescent tube, a complementary lighting means of the same strength possibly being disposed in the region of the current supply means if the annular fluorescent tube does not extend around 360°. Preferably the tube is supplied with direct current at a stabilized voltage.

The second group advantageously comprises six cameras whose optical axes are inclined for example at 80° with respect to the plane perpendicular to the axis of movement. Advantageously in this case also the optical characteristics will be selected in such a way as to give a certain overlap of the regions viewed by two adjacent cameras.

Preferably the lighting means and the two groups of cameras are mounted on a common support which is movable in respect of height to adjust the position of that assembly in dependence on the diameter of the product to be monitored and the position in respect of height of the axis of movement thereof. The product is preferably entrained horizontally along the axis of movement by at least one roller provided with a motor means, the product then preferably circulating on sliding guides. A means for displacement parallel to the axis of movement of the product makes it possible to adjust the position of the group of cameras which are inclined at 80° in order for the observed region to return the maximum light in the direction of those cameras. Automatic means advantageously make it possible to effect such adjustments on the basis of a simple display of the diameter of the products to be monitored. Advantageously the automatic means provide for adjustment and monitoring of the speed of movement of the product. Advantageously the automatic means are capable of receiving from one or more computers items of information relating to the defects detected by at least one camera and possibly items of information concerning operational incidents. Advantageously the automatic means mark the locations of defects directly in the form of marks on the surface of the product as it moves along.

It has been found that there is a reduction in the luminous intensity reflected by the regions of the perimeter of the rotationally symmetrical product, which are spaced from the optical axis of the cameras. That is particularly perceptible in the case of the cameras whose optical axis is inclined at more than 60° with respect to the plane perpendicular to the axis of movement of the product. In fact, in that case, the part of the perimeter of the product, which is viewed by each of the linear bars of those cameras, is in the shape of a highly accentuated elliptical arc. It is easily possible to determine by calculation or experiment the coefficients which have to be applied automatically by the processing means to correct the readings "niv i" which are effected on the pixels in dependence on their distance from the optical axis, the degree of inclination of that axis and the enlargement of the objective lens. It is thus possible to detect the defects in the regions which are remote from the optical axis with a degree of sensitivity comparable to that achieved in the vicinity of the optical axis.

When the product to be monitored is not rotationally symmetrical, then, as in the case of the rotationally symmetrical products referred to above, when found necessary by virtue of the shape of the product, a correction is advantageously introduced, which is particular to each shape of product, in respect of the values of "niv i" which are measured on each of the pixels which are remote from the optical axis of each camera in dependence on the spacing of those pixels with respect to the middle of the bar thereof. That correction can be determined by calculation or experiment.

Data processing in the strict sense of the signals received by the linear bars of pixels of the cameras of the first or second group, which makes it possible to determine the values of cumulative total 1 and P1 or preferably cumulative total 2 and P2 is effected by means known to the man skilled in the art. It is possible for example to use one or more computers P.C. COMPAQ (registered trademark) 486-33 or 50 MHz making it possible each to process the signals from a group of cameras and each controlled by an acquisition card or board with in addition intermediate memories for storage of the data coming from each camera.

Such a board comprises:

1) A module for production of the signals for synchronisation of the cameras, for the generation of pixel clocks and line clocks. The exposure times which are dependent on the lighting and the optical means may be for example 600 $10^{-6}$ second for the cameras which are inclined at 15° and 1200 $10^{-6}$ second for the cameras which are inclined at 80°.

2) A module for selection of N1 pixels from the N pixels of the bar. The function of this module is to validate the N1 pixels, for example 100 pixels out of the assembly N of the pixels of the bar, that is to say for example 256.

3) A module for shaping of the reading signals, which renders compatible the signals of the board and those of the bus and makes it possible to accelerate the computations, by combining the consecutive pixels on an item of 16 bit or 32 bit data.

The intermediate storage memories are advantageously formed by memory modules of the type FIFO ("first in-fist out" memory) which are interfaced with the computers and with the acquisition board or boards.

It is on the basis of the signals which are generated and shaped by the board or boards that the computing means determine the difference values indicated hereinbefore.

The calculations are carried out at the same speed as the exposures with a constant shift. The values P1 or P2 are compared at the same frequency as the exposes to defect threshold values and detection of a defect causes the intervention of the automatic marking means which provide for the production of a Eking directly on the surface of the product as it moves along.

Recording of those defects in suitable memories or by means of a printer which operates on a strip is also possible.

The process and the apparatus according to the invention can be equally advantageously applied to the detection of all types of surface defects on metallic strips of greater or lesser widths. It is possible to displace such a strip at a speed of for example 1 m/s and the surface condition is monitored by means of at least one linear camera whose optical axis is oriented in the direction of at least one of the two faces of the strip.

Depending on the strip width it is possible to provide cameras comprising a bar having 256, 512 or 1024 pixels. It is also possible if necessary to use a plurality of cameras arranged side-by-side. The lighting is advantageously provided by a straight fluorescent tube which is oriented transversely.

As in the previous case, the arrangement preferably uses at least one camera whose optical axis is inclined at not more than 30° with respect to the plane perpendicular to the axis of movement and at least one camera with an optical axis inclined at at least 60°. Finally it is possible to monitor the two faces of the strip simultaneously by disposing the cameras and lighting means required for performing that monitoring operation, on each side of the strip.

Although the industrial use of the apparatus and the process according to the invention is particularly advantageous in regard to monitoring symmetrically rotational bars or tubes of refractory or non-oxidisable metals such as stainless steels and other refractory or non-oxidisable metals, the process and the apparatus can be applied to all kinds of long products of widely different metals or alloys which may or may not be of a rotationally symmetrical profile such as bars of a square or rectangular or hexagonal section or all kinds of sections or metallic strips.

BRIEF DESCRIPTION OF THE DRAWINGS

The example and the Figures hereinafter set out a non-limiting description of a particular embodiment of the process and the apparatus according to the invention.

DETAILED DESCRIPTION OF THE PREFERRED EMBODIMENTS

Figure 1:
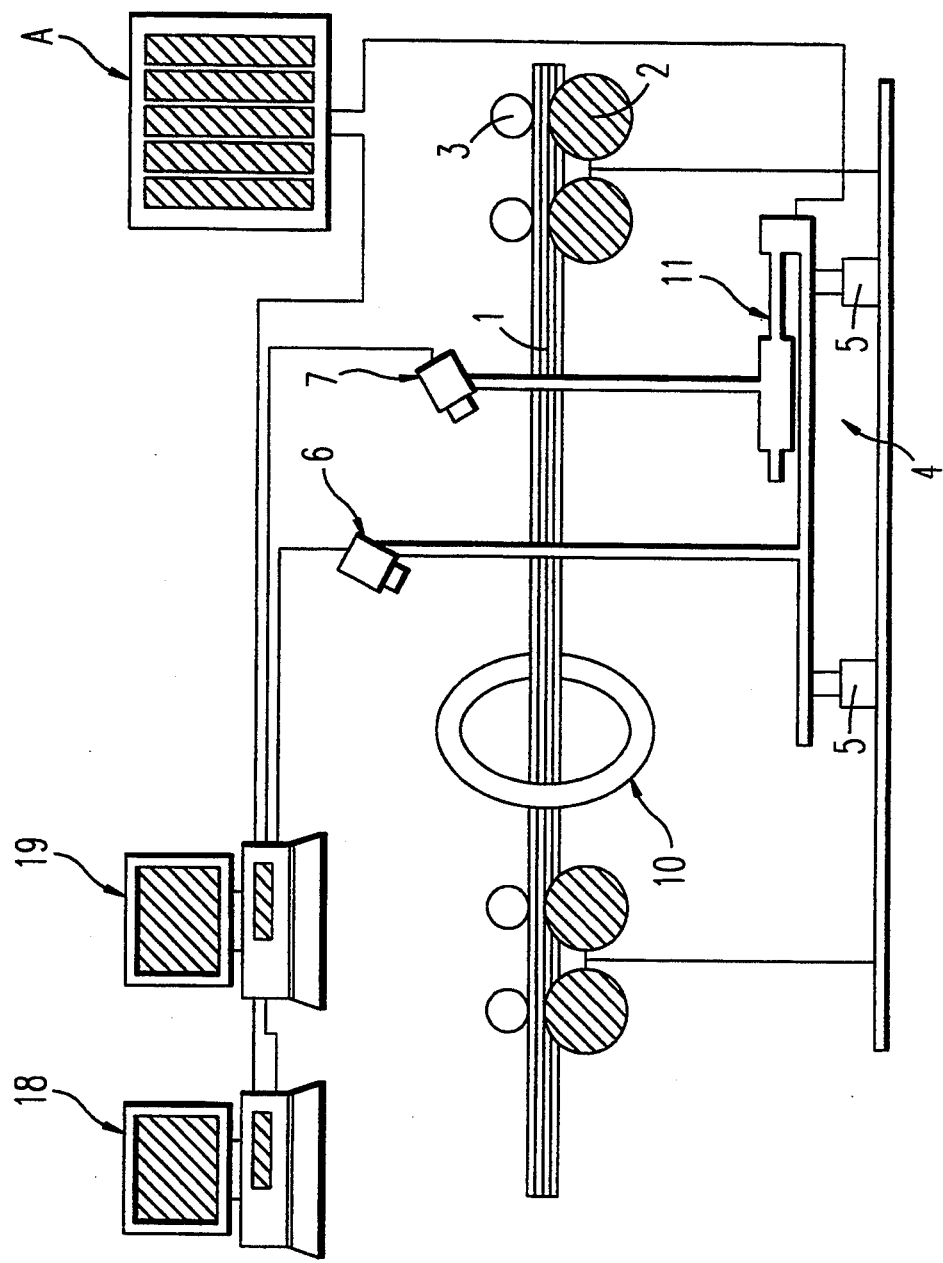
FIG. 1 is a diagrammatic elevational view of the whole of the apparatus according to the invention.

FIG. 1 is a diagrammatic elevational view of the apparatus according to the invention for carrying out the process for automatic inspection by artificial vision of long tubular products.

Figure 2:
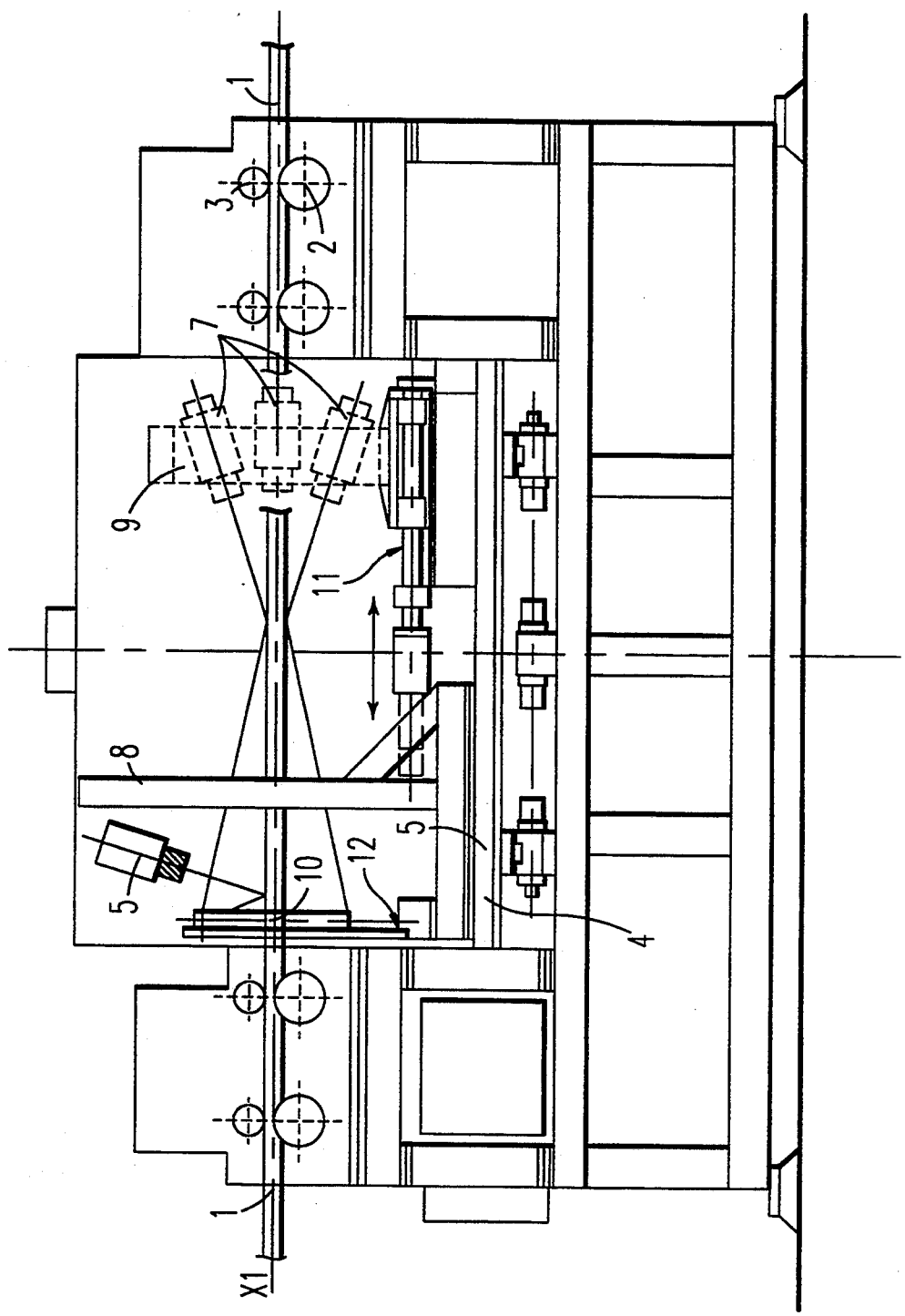
FIG. 2 is a diagrammatic elevational view of the means for entrainment of the long product and adjustment of the cameras of the apparatus according to the invention.

FIG. 2 is an elevational view, also diagrammatic, which shows in greater detail the means providing for movement of the long products to be monitored and adjustment of the inspection means. As FIG. 2 more precisely shows, the tubular product 1 circulates along an axis of movement X1—X1, entrained by rollers such as 2, 3 which hold it on its line of movement and which are themselves driven in rotation by motor means (not shown). A plate 4 which is movable vertically by way of an endless screw entrainment means 5 supports two groups of cameras 6 and 7 by way of support means 8, 9 which are diagrammatically indicated, and a means 10 for lighting the tubular product.

A group of four linear CCD cameras of which only one is indicated at 6 comprises optical axes which are inclined at 15° with respect to a plane perpendicular to the axis of movement of the product. A second group of six cameras 7 of which one is shown in FIG. 1 and three are shown in FIG. 2 comprises optical axes which are inclined at 80° with respect to a plane perpendicular to the axis of movement of the product. As FIG. 2 shows, that group is mounted on a support means 9 which is capable of sliding horizontally at 11 by virtue of entrainment means (not shown). The means for lighting the surface of the tubular product is an annular fluorescent tube 10 which is centered on the axis of movement of the product and supported by a support member 12 indicated in FIG. 2.

Figure 3:
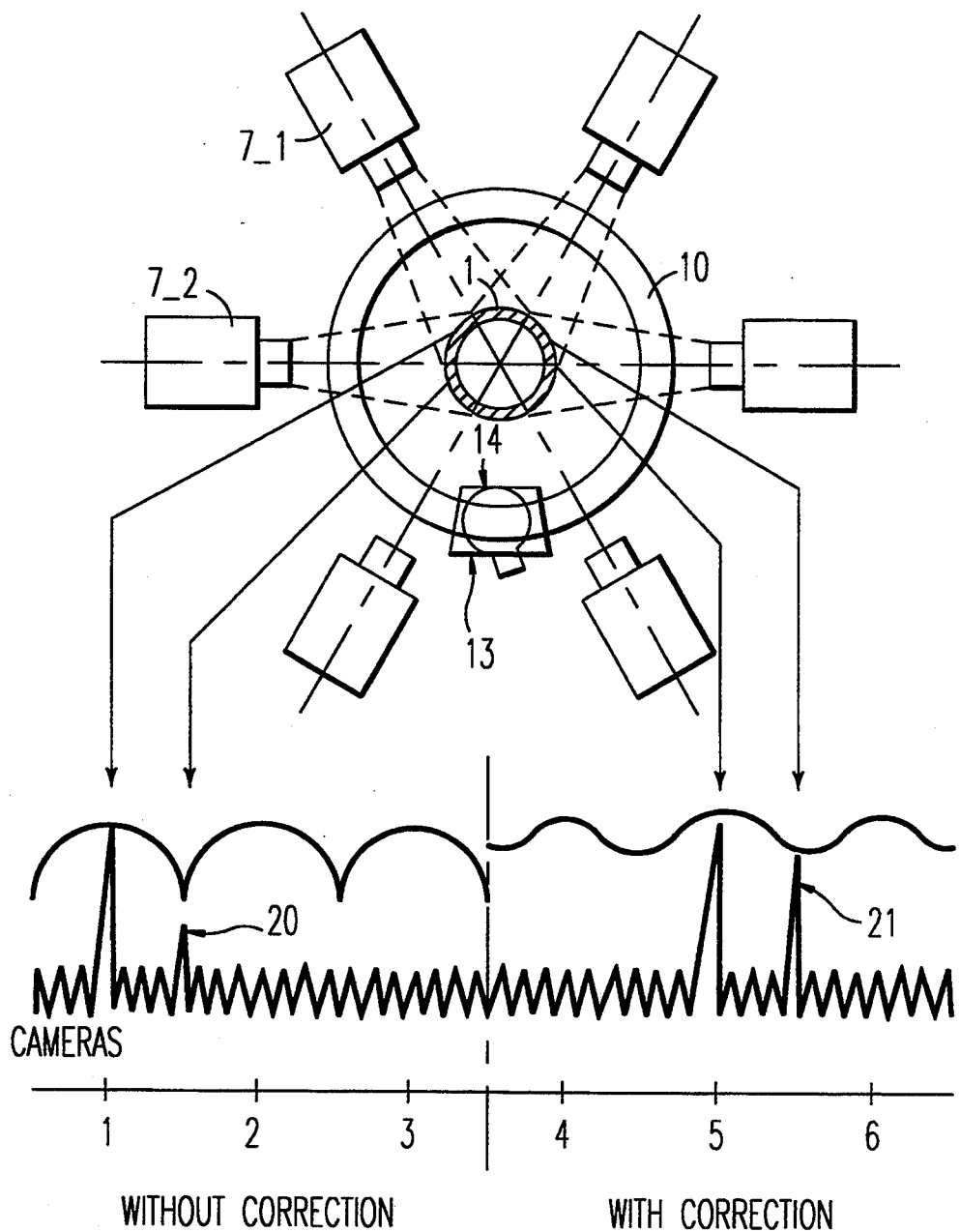
FIG. 3 is a diagrammatic front view of the group of six cameras which are inclined at 80° and the effect of the angular correction according to the invention on the detection of defects.
Figure 4:
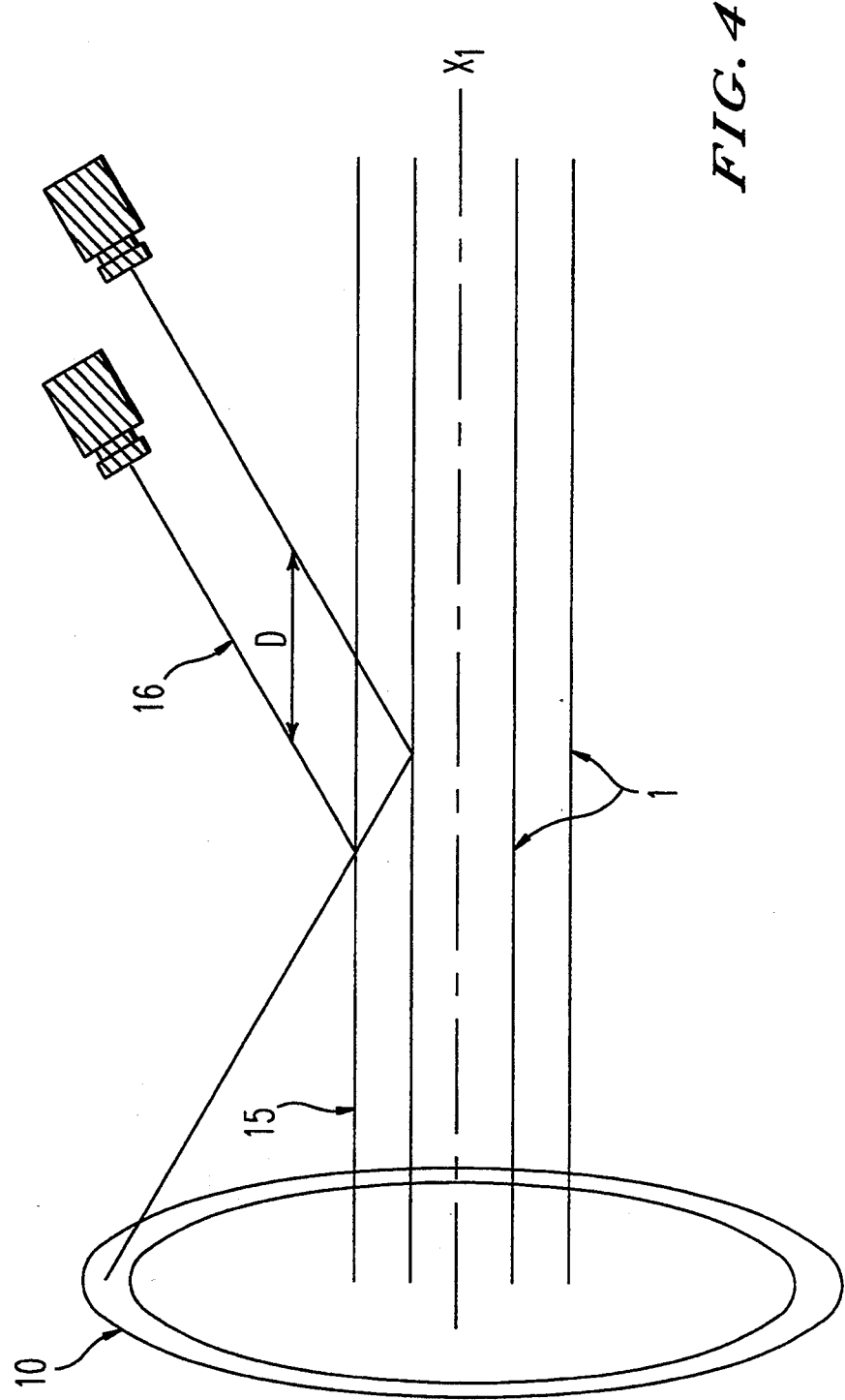
FIG. 4 is a diagrammatic view of the mode of adjustment in position of the cameras whose optical axis is at an angle which is at least equal to 60° with respect to the plane perpendicular to the axis of movement of the product.

As FIG. 3 shows, the annular tube has a non-lighting connection region 13. A remedy is afforded in that respect by placing at that location an opaline lamp 14 having a light intensity which is close to that of the fluorescent tube. The tube and the lamp are supplied with stabilised direct current. When the movable plate 4 is displaced in respect of height to take account of a variation in diameter of the tubular product to be monitored and therefore the position in respect of height of the axis of movement of the product, the rollers 2 being in a fixed position in the example illustrated, a horizontal displacement as at D (see FIG. 4) must be produced in order for the angle to be formed by the incident ray of the fluorescent tube which intersects the generatrix 15 of the tubular product 1 at the point of intersection of the optical axis 16 to be equal to the angle that that optical axis forms with that generatrix.

An automatic device A automatically effects those adjustments in respect of height and horizontal translatory movement for the group of six cameras as soon as the diameter of the tubular product to be monitored is displayed. As has been stated in the general description, the automatic device also provides for adjustment and monitoring of the speed of movement of the long product.

Figure 5:
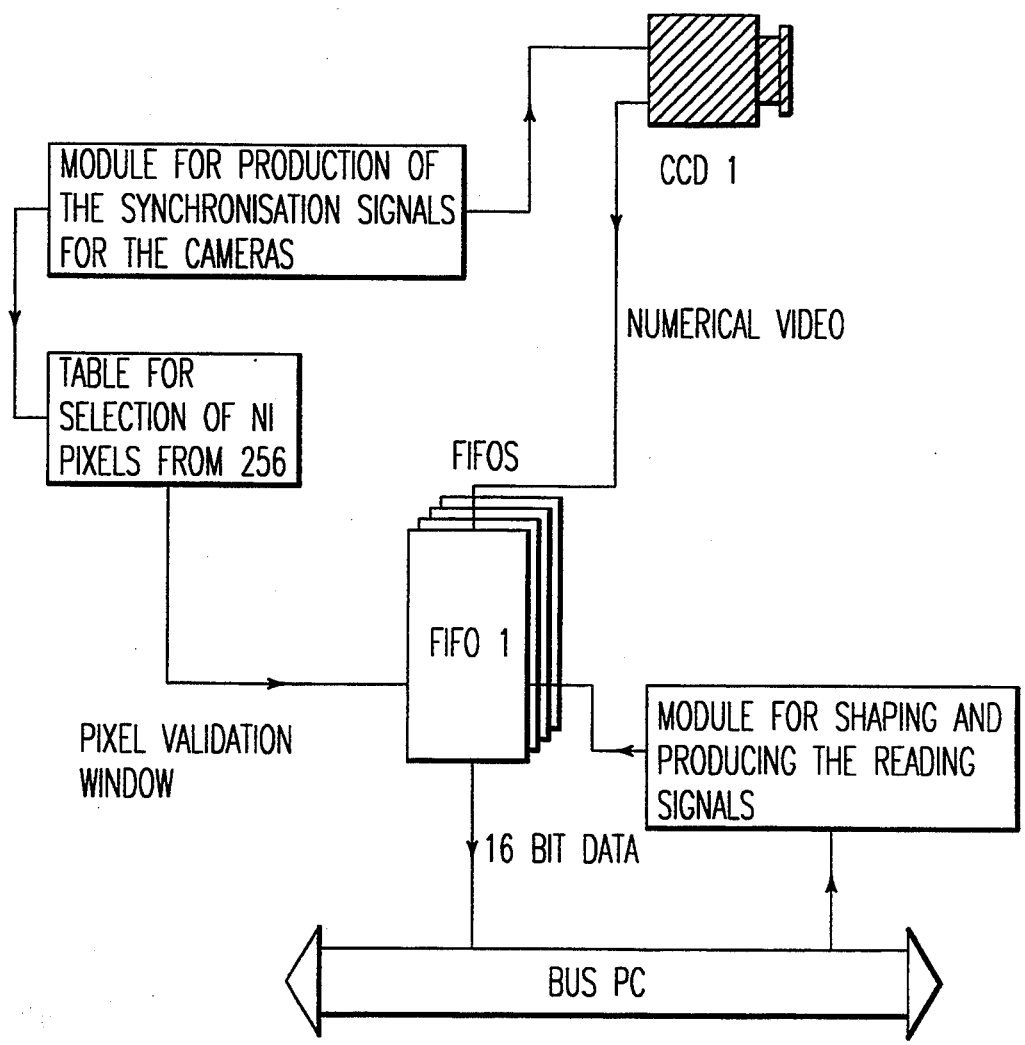
FIG. 5 shows a flow chart of an acquisition board with a memory of FIFO type for carrying out the process according to the invention.

As has also been indicated in the general description, linear CCD cameras are used in the case of the apparatus and the process which are described in the present example. Those cameras comprise a bar made up of 256 pixels of a length of 3.33 mm. In order to accelerate and standardise data processing, 100 pixels are taken, in relation to which such processing is effected. Two computers P.C. COMPAQ 486-33 MHz 18, 19 are used to carry out the program. Each of those computers is connected to a group of cameras by way of an acquisition card or board and an FIFO memory module (FIG. 5). The exposure times are $600.10^{-6}$ s for the group of four cameras and $12.00 \cdot 10^{-6}$ s for the group of six cameras. As also indicated in the general description, the processing means automatically apply correction coefficients to the readings of "niv i" which are effected on the pixels in dependence on their distance from the optical axis, the degree of inclination of that axis with respect to a plane perpendicular to the axis of movement of the product and the enlargement of the objective lens. FIG. 3 shows an example of the application of those correction coefficients to the amplitude of the defects detected.

It will be seen that a defect disposed just in the region which is remote from the optical axes of two cameras such as 7.1 and 7.2 is detected at 20. At 21, a similar defect is amplified by application of the angular correction coefficient, whereas without that amplification it is only very slightly visible.

The calculations which are performed by means of the two computers 18, 19 in accordance with the program executed for carrying out the process according to the invention make it possible to determine on the one hand the sums of the absolute values of the differences of the "niv i" for the N1 pixels at two successive exposure times such as t1, t2: this is the value cumulative total 1. By deducting two successive values of cumulative total 1, that gives, as was explained previously, a value "P1" which can be referred to as "combined difference in terms of absolute value". As will be seen, that value "P1" suffers from the disadvantage of involving a substantial degree of dispersion and it can be of only little significance.

The method developed on the basis thereof, as the example hereinafter shows, is much more effective. It was firstly found that, on a tubular product of stainless steel without visible defect, the readings of "niv i" can be adjusted for example to a mean value of about 100 with variations which are referred to as background noise of between 70 and 130. It is therefore desirable to limit the read values of "niv i" by a threshold in the vicinity of 70 or 80 in order to eliminate the influence of that background noise. Those values of 70 and 80 are the "grey thresholds" which were introduced in the general description of the invention. When that has been done, the sums of the algebraic differences are calculated, and that is "cumulative total 2", as was explained hereinbefore, and, by a difference in two successive values of cumulative total 2, the combined difference P2 is determined.

The three tables hereinafter show the results obtained in the case of different specimens of tube of chrome nickel stainless steel of the type AISI 304.

Each of those three tables shows the values of "niv i" which are measured on a consecutive series of ten exposures at the times t1 to t10 on a group of 15 pixels taken from the 100 pixels which are the subject of data processing of a bar of 256 pixels. The camera used is part of the group of four cameras which are inclined at 15° for observing stains or blemishes. Below the columns of 15 numeral values "niv i" each corresponding to a pixel, the following are successively indicated:

1) The values of cumulative total 1, the sum of the absolute differences between the values "niv i" at the times t2-t1, t3-t2, t4-t3 ... t10-t9.

2) The value of P1, the difference between two consecutive values of cumulative total 1, the difference being taken in terms of absolute value.

3) The value of cumulative total 2, the sum of the differences in terms of algebraic value in "niv i" at the times t2-t1, t3-t2, ... t10-t9, for a "grey threshold" of 80.

4) The corresponding value of P2, the difference between two consecutive values of cumulative total 2, taken in terms of absolute value.

5) The value of cumulative total 2, the sum of the differences in terms of absolute value in "niv i" at the times t2-t1, t3-t2, ... t10-t9, for a "grey threshold" of 70.

6) The corresponding value of P2, the difference between two consecutive values of cumulative total 2, taken in terms of absolute value.

TABLE I

| t1 | t2 | t3 | t4 | t5 | t6 | t7 | t8 | t9 | t10 | exposure time |
|---|---|---|---|---|---|---|---|---|---|---|
| 101 | 79 | 88 | 103 | 130 | 79 | 114 | 82 | 100 | 76 | |
| 73 | 93 | 86 | 92 | 132 | 103 | 118 | 110 | 118 | 119 | |
| 121 | 77 | 108 | 88 | 90 | 128 | 102 | 94 | 107 | 119 | |
| 129 | 125 | 124 | 112 | 117 | 106 | 93 | 91 | 81 | 122 | |
| 95 | 98 | 132 | 76 | 81 | 130 | 116 | 94 | 119 | 117 | |
| 130 | 69 | 88 | 117 | 83 | 106 | 70 | 130 | 88 | 71 | |
| 96 | 127 | 105 | 75 | 105 | 84 | 100 | 83 | 99 | 94 | |
| 125 | 95 | 91 | 93 | 70 | 78 | 102 | 113 | 74 | 94 | |
| 118 | 84 | 90 | 83 | 87 | 87 | 126 | 70 | 110 | 94 | |
| 112 | 116 | 129 | 83 | 122 | 131 | 119 | 96 | 112 | 121 | |
| 78 | 86 | 76 | 124 | 117 | 81 | 77 | 87 | 120 | 82 | |
| 104 | 114 | 80 | 132 | 84 | 96 | 117 | 124 | 126 | 132 | |
| 93 | 96 | 76 | 97 | 83 | 132 | 110 | 107 | 83 | 97 | |
| 119 | 73 | 99 | 78 | 84 | 129 | 108 | 132 | 99 | 120 | |
| 116 | 92 | 99 | 102 | 74 | 106 | 90 | 77 | 119 | 114 | |
| | 344 | 243 | 368 | 312 | 413 | 314 | 296 | 361 | 231 | Cumulative total 1 |
| | | 101 | 125 | 56 | 101 | 99 | 18 | 65 | 130 | P1 |
| | −13 | 14 | −3 | −5 | 13 | −10 | 0 | 7 | −7 | Cumulative total 2 |
| | | 27 | 17 | 2 | 18 | 23 | 10 | 7 | 14 | P2 threshold - 80 |
| | −1 | 1 | 0 | 0 | 0 | 0 | 0 | 0 | 0 | Cumulative total 2 |
| | | 2 | 1 | 0 | 0 | 0 | 0 | 0 | 0 | P2 threshold - 70 |

TABLE II

| t1 | t2 | t3 | t4 | t5 | t6 | t7 | t8 | t9 | t10 | exposure time |
|---|---|---|---|---|---|---|---|---|---|---|
| 101 | 79 | 88 | 103 | 130 | 79 | 114 | 82 | 100 | 76 | |
| 73 | 93 | 86 | 92 | 132 | 103 | 118 | 110 | 118 | 119 | |
| 121 | 77 | 108 | 88 | 90 | 128 | 102 | 94 | 107 | 119 | |
| 129 | 125 | 124 | 112 | 117 | 106 | 93 | 91 | 81 | 122 | |
| 95 | 98 | 132 | 76 | 81 | 130 | 116 | 94 | 119 | 117 | |
| 130 | 69 | 88 | 117 | 83 | 106 | 70 | 130 | 88 | 71 | |
| 68 | 83 | 72 | 57 | 72 | 62 | 70 | 61 | 69 | 67 | |
| 82 | 67 | 65 | 66 | 55 | 59 | 71 | 76 | 57 | 67 | Welding |
| 79 | 62 | 65 | 61 | 63 | 63 | 83 | 55 | 75 | 67 | |
| 112 | 116 | 129 | 83 | 122 | 131 | 119 | 96 | 112 | 121 | |
| 78 | 86 | 76 | 124 | 117 | 81 | 77 | 87 | 120 | 82 | |
| 104 | 114 | 80 | 132 | 84 | 96 | 117 | 124 | 126 | 132 | |
| 93 | 96 | 76 | 97 | 83 | 132 | 110 | 107 | 83 | 97 | |
| 119 | 73 | 99 | 78 | 84 | 129 | 108 | 132 | 99 | 120 | |
| 116 | 92 | 99 | 102 | 74 | 106 | 90 | 77 | 119 | 114 | |
| | 296 | 227 | 349 | 283 | 398 | 275 | 254 | 313 | 210 | Cumulative total 1 |
| | | 69 | 122 | 66 | 115 | 123 | 21 | 59 | 103 | p1 |
| | −31 | 7 | −16 | 6 | −1 | 25 | −19 | 12 | −13 | Cumulative total 2 |
| | | 38 | 23 | 22 | 7 | 26 | 44 | 31 | 25 | p2 threshold - 80 |
| | −10 | 2 | −16 | 4 | −4 | 26 | −24 | 10 | 5 | Cumulative total 2 |
| | | 12 | 18 | 20 | 8 | 30 | 50 | 34 | 5 | p2 threshold - 70 |

TABLE III

| t1 | t2 | t3 | t4 | t5 | t6 | t7 | t8 | t9 | t10 | exposure time |
|---|---|---|---|---|---|---|---|---|---|---|
| 101 | 79 | 88 | 103 | 130 | 79 | 114 | 82 | 100 | 76 | |
| 73 | 93 | 86 | 92 | 132 | 103 | 118 | 110 | 118 | 119 | |
| 121 | 77 | 108 | 85 | 90 | 128 | 102 | 94 | 107 | 119 | |
| 129 | 125 | 124 | 112 | 117 | 106 | 93 | 91 | 81 | 122 | |
| 95 | 98 | 132 | 76 | 81 | 130 | 116 | 94 | 119 | 117 | |
| 130 | 69 | 88 | 117 | 83 | 106 | 70 | 130 | 88 | 71 | |

TABLE III-continued

| t1 | t2 | t3 | t4 | t5 | t6 | t7 | t8 | t9 | t10 | exposure time |
|---|---|---|---|---|---|---|---|---|---|---|
| 68 | 83 | 72 | 57 | 72 | 62 | 70 | 61 | 69 | 67 | |
| 82 | 67 | 65 | 66 | 55 | 59 | 71 | 76 | 57 | 67 | |
| 79 | 62 | 65 | 61 | 63 | 63 | 83 | 55 | 75 | 67 | |
| 112 | 116 | 129 | 83 | 122 | 131 | 119 | 96 | 112 | 121 | |
| 78 | 86 | 76 | 124 | 117 | 81 | 77 | 87 | 120 | 82 | |
| 104 | 114 | 80 | 132 | 42 | 96 | 117 | 124 | 126 | 132 | |
| 93 | 96 | 76 | 97 | 41 | 132 | 110 | 107 | 83 | 97 | |
| 119 | 73 | 99 | 78 | 84 | 129 | 108 | 132 | 99 | 120 | |
| 116 | 92 | 99 | 102 | 74 | 106 | 90 | 77 | 119 | 114 | |
| | 296 | 227 | 349 | 367 | 482 | 275 | 254 | 313 | 210 | Cumulative total 1 |
| | | 69 | 122 | 18 | 115 | 207 | 21 | 59 | 103 | p1 |
| | −31 | 7 | −16 | −71 | 76 | 25 | −19 | 12 | −13 | Cumulative total 2 |
| | | 38 | 23 | 55 | 147 | 51 | 44 | 31 | 25 | p2 threshold - 80 |
| | −10 | 2 | −16 | −53 | 53 | 26 | −24 | 10 | 5 | Cumulative total 2 |
| | | 12 | 18 | 37 | 106 | 27 | 50 | 34 | 5 | p2 threshold - 70 |

The values of cumulative total 2 and P2 are calculated for two values of "grey thresholds" of 80 and 70 in order better to show the influence of elimination of the background noise.

The results of table I which corresponds to a region which is free from defects show that there is a dispersion of the values "niv i" due to the dispersion of the conditions of reflection of the light by a metallic surface, even one which is free from defects. In the case of this table the values of "niv i" are approximately 100±30. The values of cumulative total 1 and P1 show that dispersion. It is noted in particular that P1 varies between 18 and 125 in spite of absence of stains or blemishes.

That dispersion disappears by virtue of the introduction of the thresholds and the algebraic differences. For a "grey threshold" of 80, there then remains nothing more than a low degree of dispersion of the values of cumulative total 2 and P2 and for a "grey threshold" of 70 that dispersion completely disappears.

Table II shows a region without defects but comprising a longitudinal welding line. That is visible by virtue of a slight degree of colouring which reduces the values of "niv i" over a width of three pixels. The use of "grey thresholds" of 80 and 70 and the algebraic differences considerably attenuates the degree of dispersion of the values of cumulative total 2 and P2. The continuous welding line does not cause any discontinuity to appear in the values of P2.

Table III shows a region comprising like table II, longitudinal welding and in addition a localized surface defect (stain). This time, the stain region which is marked by boxing in the table is visible by virtue of the low values of "niv i" at the exposure time t5 and is particularly clearly observed at the level of the values P2.

It appears from the results of these three examples that the method for processing of the values of "niv i" which has thus been described makes it possible clearly to show the regions of localised defects on the long products while removing the influence on the method of measurement of continuous longitudinal regions such as the welding region. It is only necessary to choose a "defect threshold" S associated with each "grey threshold" and to compare the values obtained for P2 to S: if P2>S the tube being monitored will be considered as having a defect.

S will be selected after calibration of the method and the items of equipment used.

In the examples proposed in tables I, II and III, it will be possible for example to take the following as the defect threshold:

S=60 for the "grey threshold"=80
S=55 for the "grey threshold"=70

Those defects are then marked on the products and-/or are recorded in such a way as to provide for effective monitoring over the entire length of the product.

Similar monitoring operations are carried out by means of the cameras whose optical axes are inclined at 80° for searching for scratches, cracks or other changes in level. Here also, the measurements of cumulative total 2 and P2 are particularly significant.

As indicated above the apparatus and the process according to the invention can be applied to the detection of all types of surface defects on strips and all kinds of shaped members.

A very large number of modifications may be made in the process and the apparatus which are the subject of the invention without departing from the scope thereof.

In particular, instead of effecting processing of the values of "niv i" and cumulative total 1, P1 and cumulative total 2, P2 on an assembly of N1 pixels, it is possible to divide those N1 pixels into a plurality of successive zones or partially overlapping zones of N2 pixels each and effect processing of the values of "niv i", cumulative total 1, P1 and cumulative total 2, P2 separately in respect of those zones of N2 pixels.

That therefore involves working on smaller and more numerous zones and that makes it possible to achieve a higher degree of sensitivity and better to eliminate the background noise, in particular in cases where the product involves irregular reflectiveness, although without that corresponding to surface defects in the true sense.

It is also possible to carry out the process according to the invention by using a matrix-type CCD camera comprising a plurality of parallel lines of bars, in place of a linear CCD camera comprising a single bar.

Insofar as the items of information extracted from those lines of bars are used as in the present invention line by line, the matrix-type CCD camera will then be considered as a linear CCD camera, such a matrix-type camera then falling within the scope of the present invention.

We claim:

1. A process for detecting surface defects on extended metallic products moving along an axis through the use of at least one linear CCD camera having a bar formed by line of N pixels (i1, i2, i3, . . . in) orientated transversely with respect to the axis of movement of the product and said camera including an optical means for viewing an illuminated region of the surface of the product in order to form an image of the region on the bar of pixels and utilizing an entrainment means for moving the product along its axis of movement at a given speed, said process comprising the steps of:

connecting said camera to data acquisition and processing means which data and processing means permits measurement of numerical values niv i at equal successive exposure intervals t1, t2, t3 ... tn, said numerical values corresponding to the amounts of light which are received by each pixel i1, i2, i3 ... iN1 of an assembly of N1 pixels selected from the N pixels of the bar with N1<N;

calculating differences between said numerical values for each pixel i at two successive exposure times (t1, t2);

determining the sum of said differences for all of said N1 pixels; and detecting the presence of defects as a function of changes in said sum as said product moves along said axis.

2. A process according to claim 1 wherein the sum of the differences in the levels of each pixel "niv i" for the assembly of N1 pixels of a bar, which levels are measured at two successive exposure times, is a first cumulative total value 1 corresponding to the sum of the absolute values of said differences.

3. A process according to claim 1 wherein the numerical value "niv i" of each pixel is limited to a threshold value, referred to as the "grey threshold", all the higher values determined on the basis of the amounts of light which are received by any pixel being automatically reduced to that threshold value for the calculations of differences.

4. A process according to claim 3 wherein the sum of the differences in the levels of each pixel "niv i" for the assembly of N1 pixels of a bar, at two successive times, is a second cumulative total value 2 corresponding to the sum of the algebraic values of said differences.

5. A process according to claim 3 wherein the "grey threshold" is limited to about 70 to 80% of the mean value of the values "niv i" for the regions of the long products which are free from stains and defects.

6. A process according to claim 2 wherein, on the basis of the values of cumulative total 1 which are calculated at successive times t1, t2, t3 ..., there is determined a combined difference value P1 taken in terms of absolute value such that:

$$P1 = |\text{cumulative total } 1 \ (t3\text{-}t2) - \text{cumulative total } 1 \ (t2\text{-}t1)|,$$

a variation in said combined difference value P1 providing an indication of defects to be detected.

7. A process according to one of claims 3, 4 or 5 wherein, on the basis of the successive values of cumulative total 2 which are calculated at times t1, t2, t3 ..., there is determined a combined difference value P2 taken in terms of absolute value such that:

$$P2 = |\text{cumulative total } 2 \ (t3\text{-}t2) - \text{cumulative total } 2 \ (t2\text{-}t1)|,$$

a variation in said combined difference value P2 providing an indication of defects to be detected.

8. A process according to claim 1 wherein there is used at least one linear CCD camera whose optical axis is so oriented that it does not form an angle of greater than about 30° with respect to a plane perpendicular to the axis of movement.

9. A process according to claim 1 wherein there is used at least one linear CCD camera whose optical axis is so oriented that it does not form an angle of less than about 60° with respect to a plane perpendicular to the axis of movement.

10. A process according to claim 1 wherein lighting of the region viewed by at least one camera is effected by at least one light source which is supplied with stabilised-voltage direct current.

11. A process according to claim 1 wherein, when the long product is a rotationally symmetrical product, there are provided at least four linear CCD cameras distributed around the axis of movement of the product, each having an optical axis inclined at less than 30° with respect to a plane perpendicular to the axis of movement of the product and at least six linear CCD cameras distributed around the axis of movement of the product each having an optical axis inclined at at least 60° with respect to a plane perpendicular to the axis of movement of the product.

12. A process according to claim 1 wherein the number of N1 pixels is determined in such a way as to permit data processing of the N1 numerical values during the time of an exposure and that, in the case of products of relatively great width, the N1 pixels are distributed over the width of the region of the bar of pixels which is occupied by the image, the other pixels whether they are or are not in the image region not being processed.

13. A process according to claim 1 wherein, in the case involving the use of at least one camera whose optical axis is inclined at an angle of not less than 60° with respect to a plane perpendicular to the axis of movement of the product, the exposure time is increased in dependence on the reduction in the intensity of lighting of the bar of pixels and its optical characteristics with respect to the case involving a camera whose optical axis is at a smaller angle to said plane perpendicular to the axis of movement.

14. A process according to claim 1 wherein a correction in respect of the numerical values "niv i" which are measured on each of the pixels which are remote from the optical axis of each camera is effected in dependence on the spacing of said pixels with respect to the middle of the bar thereof.

15. A process according to claim 14 wherein, in the case involving detection of defects on rotationally symmetrical products, a correction in respect of the numerical values "niv i" which are measured on each of the pixels which are remote from the optical axis of each camera is effected in dependence on the spacing of said pixels with respect to the middle of the bar thereof, the diameter of the rotationally symmetrical product, the enlargement of the objective lens and the inclination of the optical axis of the camera with respect to the plane perpendicular to the axis of movement of the product to compensate for the lesser amount of light which is received by said pixels.

16. A process according to claim 1 wherein the N1 pixels are divided into a plurality of successive or partially overlapping zones of N2 pixels each and that processing of the values of "niv i", cumulative total 1, P1, cumulative total 2 and P2 is effected separately on each zone of N2 pixels.

17. An apparatus for detecting surface defects on a long metallic product moved along an axis and including at least one linear CCD camera having a bar formed by a line of N pixels oriented transversely with respect to the axis of movement of the product, said apparatus comprising:

an optical means for forming on the bar of pixels an image of at least one region of a surface of the product;

a lighting means for lighting said region; and an entrainment and guide means for passing the product along said axis of movement at a given speed;

a means for producing camera synchronization signals for generating pixel clocks and line clocks of said camera in order to determine exposure times;

memory means for storing data;

data processing means for calculating cumulative differences between numerical values of lightings received by said pixels at successive exposure times;

detecting means for detecting defects along the product as it moves on said axis as a function of one of the algebraic or absolute values of said cumulative differences.

18. Apparatus according to claim 17 further comprising at least two linear CCD cameras, the optical axis of one (6) being inclined by not more than 30° with respect to a plane perpendicular to the axis of movement of the product and the other (7) having its axis inclined by at least 60° with respect to said same plane.

19. Apparatus according to claim 17 wherein, when the product is a rotationally symmetrical product, it comprises two groups of CCD cameras, the first group (6) comprising four cameras which are distributed around the axis of movement and the optical axis of which is inclined by not more than 30° with respect to a plane perpendicular to the axis of movement and the other (7) comprising at least six cameras which are distributed around the axis of movement and the optical axis of which is at an angle which is at least equal to 60° with respect to a plane perpendicular to said axis of movement.

20. Apparatus according to claim 19 wherein the means for lighting the surface of the rotationally symmetrical product is an annular fluorescent tube (10).

21. Apparatus according to claim 19 wherein, in order to permit monitoring of products of different diameters, the assembly comprising the annular lighting means and the two groups of cameras is fixed with respect to a platform (4) which is displaceable vertically by way of a motor means.

22. Apparatus according to claim 21 further comprising a means (11) for displacement parallel to the axis of movement of the product of the group of cameras with their optical axis inclined at at least 60° with respect to a plane perpendicular to the axis of movement of the product which is connected to the vertically displaceable platform in order to obtain the maximum lighting effect for each product diameter.

23. Apparatus according to one of claims 19 to 22 wherein that the means for entrainment of the rotationally symmetrical product along the axis of movement is formed by motorised rollers (2, 3).

24. Apparatus according to claim 17 or claim 18 wherein when the long product in movement is a metallic strip which is simultaneously monitored on its two faces, it comprises two groups of at least two linear CCD cameras, the first group comprising at least two cameras with the optical axis inclined by not more than 30° with respect to a plane perpendicular to the axis of movement and which are disposed on respective sides of the strip and the second group comprising at least two cameras with the optical axis inclined by at least 60° with respect to said same plane perpendicular to the axis of movement and which are disposed on respective sides of the strip.

* * * * *